United States Patent [19]
Hill

[11] 3,969,077
[45] July 13, 1976

[54] ALKALI METAL LEAK DETECTION METHOD AND APPARATUS

[75] Inventor: Eugene F. Hill, Belmont, Calif.

[73] Assignee: Varian Associates, Palo Alto, Calif.

[22] Filed: Mar. 13, 1974

[21] Appl. No.: 450,625

Related U.S. Application Data

[63] Continuation of Ser. No. 208,733, Dec. 16, 1971, abandoned.

[52] U.S. Cl. ............................ 23/230 L; 23/232 E; 23/254 E; 176/19 R; 176/37
[51] Int. Cl.² ................. G01N 31/00; G01N 33/20
[58] Field of Search ........... 23/230 L, 254 E, 255 E, 23/232 E; 324/33; 73/40, 40.5 R; 176/19 LD, 19 R, 37

[56] References Cited
UNITED STATES PATENTS

| | | | |
|---|---|---|---|
| 2,787,903 | 4/1957 | Beard | 73/23 |
| 3,631,436 | 12/1971 | Taguchi | 23/254 E X |
| 3,683,272 | 8/1972 | Vissers | 324/33 |
| 3,721,116 | 3/1973 | Brachet et al. | 73/40 |

*Primary Examiner*—Robert M. Reese
*Attorney, Agent, or Firm*—Stanley Z. Cole; Leon F. Herbert

[57] ABSTRACT

A method and apparatus for detecting a leak of an alkali metal in liquid form in a structure such as the heat transfer system of a nuclear reactor. When alkali metal leaks from its containment structure and thereupon comes into contact with a compound containing hydrogen which can be displaced by the alkali metal, a chemical reaction occurs by which hydrogen gas is generated. The hydrogen gas so generated will diffuse very rapidly throughout the region proximate to the sodium leak. The hydrogen compound can be present in a variety of physical forms. The compound barium hydroxide is especially suitable as a source for the generation of hydrogen gas. Water vapor in air or in an inert gas also provides a suitable hydrogen source. A sensor located within the region of the alkali metal leak will sense the presence of hydrogen gas and will thereupon activate an alarm or recording device. The efficiency of the leak detection system can be evaluated and periodically tested by simply introducing a measured quantity of hydrogen gas into the region proximate to the alkali containment structure. This obviates the necessity of effecting a controlled alkali metal leak in order to test the leak detection system.

25 Claims, 4 Drawing Figures

ALKALI METAL LEAK DETECTION METHOD AND APPARATUS

This is a continuation of application Ser. No. 208,733, filed Dec. 16, 1971.

BACKGROUND OF THE INVENTION

1. Field of the Invention

This invention is a further development in the field of alkali metal leak detection, particularly with respect to liquid sodium heat transfer systems for nuclear reactors.

2. Description of the Prior Art

A number of techniques have been developed to detect a sodium leak in the coolant system of a nuclear reactor. The most common technique at the present time involves the placement of a pair of electrodes, separated from one another by a suitable gap, in proximity to the sodium containment structure. When a sodium leak occurs, sodium will condense or flow onto the electrodes and will eventually cause a short circuit between the electrodes. This short circuit will activate an alarm or recording device. There are two major deficiencies inherent in this technique. First, the path of the condensing or flowing sodium after it leaks from its containment structure is unpredictable, and there is no assurance that the leaking sodium will ever come into contact with the electrodes to produce a short circuit. Second, the electrodes are sensitive to short-circuiting by materials other than leaking sodium, which presents the possibility of false leak alarms.

Another technique involves the impingement of light from a sodium vapor lamp onto a photoelectric cell in the vicinity of the sodium containment structure. When sodium leaks from the containment structure, the sodium atoms "cloud" the region between the sodium vapor lamp and the photoelectric cell. The sodium atoms in the cloud absorb light from the lamp, thereby reducing the intensity of the light impinging upon the photoelectric cell. The reduction in intensity of the light impinging on the photoelectric cell can be sensed to activate a leak alarm or recorder. However, at least one of the deficiencies inherent in the short-circuiting technique described above is likewise inherent in this atomic absorption technique. The leaking sodium can condense on surfaces external to the containment structure and never travel to the region between the lamp and the photoelectric cell. The unpredictability of the path of the leaking sodium renders both the short circuiting technique and the atomic absorption technique ineffective in assuring rapid detection of a sodium leak.

Another technique involves confinement of the atmosphere in the region proximate to the external surface of the sodium containment structure, and the forcing of this confined atmosphere into water solution at regular intervals. Any sodium which has leaked into this region, whether it remains in pure form or has oxidized, will cause the water to become alkaline. The pH of the water can be monitored, and a change in pH can cause the activation of an alarm or recording device. The main problem with this technique, aside from its requirement for extensive ancillary equipment, is that it is not sufficiently sensitive to detect minute sodium leaks. Minute changes in pH of a large volume of water are difficult to detect. Furthermore, leaking sodium can condense on structural surfaces without mixing in the confined atmosphere that will pass into water solution for pH testing.

Still another technique involves monitoring the oxygen gas content of a confined atmosphere in the vicinity of the sodium containment structure. Leaking sodium will react chemically with the oxygen gas, and thereby reduce the amount of oxygen gas in the atmosphere. The main problem with this technique is that it is not sufficiently sensitive to detect minute sodium leaks. Extremely small changes in the oxygen gas content of a large volume of monitored atmosphere are difficult to detect.

Existing sodium leak detection techniques are not amenable to calibration and checking for positive reliability without causing sodium to enter the detection system. A controlled sodium leak is difficult to achieve, particularly because of the unpredictability of the path the leaking sodium will take. Since it is difficult to remove all traces of sodium from the detection system after an efficiency test of the system, it is very undesirable to test the effectiveness of present sodium leak detection systems.

SUMMARY OF THE INVENTION

This invention provides an improved method and apparatus for detecting an alkali metal leak, such as in the heat transfer system of a sodium-cooled nuclear reactor. The invention involves the presence of a suitable hydrogen compound in communication with the external surfaces of the alkali metal containment structure, and the disposition of a sputter-ion pump probe fitted with a hydrogen-permeable diaphragm in the vicinity of the alkali metal containment structure. Upon the occurrence of a leak, a chemical reaction will take place which will generate hydrogen gas. The hydrogen gas so generated will, because of its rapid mobility, quickly reach and diffuse through the hydrogen-permeable diaphragm of the sputter-ion pump probe. The increased pressure within the sputter-ion pump produced by the entering hydrogen gas will cause an alarm or recording device to be activated.

It has been found experimentally that, where the external surface of a sodium containment structure is in communication with an air or inert gas atmosphere, there will be sufficient water vapor present to sustain the generation of a detectable amount of hydrogen gas upon the leakage of sodium into such an atmosphere, even where the dew point of the air or inert gas is as low as −45°F.

In situations where the presence of air or inert gas with sufficient water content cannot be anticipated the invention provides for disposing some other hydrogen containing substance in a location where it will be contacted by alkali metal which leaks out of its containment structure.

It has been found experimentally that the compound barium hydroxide, $Ba(OH)_2$ or $BaO·H_2O$, is especially suitable as a hydrogen gas generating source in the vicinity of a nuclear reactor. Barium hydroxide is chemically stable to temperatures of up to 700°C, which is well above the range at which nuclear reactors typically operate. Barium hydroxide is also stable under the radiation fluxes associated with nuclear reactors. In addition, barium hydroxide will react with sodium, the alkali metal normally used in nuclear reactors, over the entire range of temperatures at which a nuclear reactor typically operates, yet it will not react corrosively with stainless steel or other high-temperature ferrous alloys at these temperatures. Thus, barium hydroxide is particularly compatible with the sodium containment structures of a nuclear reactor coolant system, and furthermore is inert with respect to the silicates or oxides normally used as insulating materials.

In situations where ambient, non-isotopic, hydrogen gas might normally be expected to be present in the vicinity of the alkali metal containment structure even in the absence of a leak, it becomes necessary to provide a system which detects only that hydrogen gas which is generated by alkali metal leaking from the containment structure. Hydrogen gas resulting from the leak is distinguished from the ambient hydrogen by disposing a compound containing a hydrogen isotope in the vicinity of the alkali metal containment structure, and by coupling the sputter-ion or other vacuum pump to a mass spectrometer. Leaking alkali metal will generate a quantity of isotopic hydrogen gas greatly in excess of the amount of isotopic hydrogen normally found in the atmosphere, and this excess can readily be detected by the mass spectrometer. Barium deuteroxide (i.e., barium hydroxide with a heavy hydrogen atom) is readily available and is especially suitable as an isotopic hydrogen generating source in the vicinity of a nuclear reactor. The stability characteristics of barium deuteroxide are comparable to those of barium hydroxide.

The permeability of the diaphragm through which the hydrogen gas diffuses into the vacuum system connected to the diaphragm is a function of the temperature of the diaphragm. Thus the measurement of hydrogen gas diffusing through the diaphragm will be a correct measurement of the concentration of hydrogen gas outside the diaphragm only if the system is calibrated for the temperature of the diaphragm. This is done by either maintaining the temperature of the diaphragm constant by use of a heater, or monitoring the temperature of the diaphragm and adjusting the pressure signal by means of a temperature compensating signal.

It is an object of this invention to provide detection of an alkali metal leak from a containment structure by sensing hydrogen gas generated by the leaking alkali metal. In particular, it is an object of this invention to provide detection of a sodium leak as aforesaid by a hydrogen gas sensing device disposed to sense hydrogen gas that is generated by the displacement of hydrogen from a hydrogen compound.

Another object of the invention is to add a hydrogen containing substance adjacent to the outside of the alkali metal containment structure to provide an assured source of hydrogen. A related object is to add a source of isotopic hydrogen to permit distinction between ambient non-isotopic hydrogen and the hydrogen which is caused by a leak.

Another object of the invention is to provide an efficient and inexpensive system employing an ion pump as the combined vacuum source and pressure measuring source in the detection system of the invention.

A further object of the invention is to provide a system which includes consideration of the temperature of the hydrogen-permeable diaphragm in order to give an output signal which is truly representative of hydrogen gas concentration outside the diaphragm.

It is also an object of this invention to provide a rapid indication of the existence of a sodium leak, without requiring the leaking sodium to condense upon or come into contact with the leak detection apparatus.

In addition to the foregoing it is an object of this invention to provide for detecting an alkali metal leak from a containment structure, whereby the leak detection apparatus can be calibrated and tested without the necessity of effecting a controlled leak or any leak at all.

DETAILED DESCRIPTION OF THE INVENTION

Figure 1:
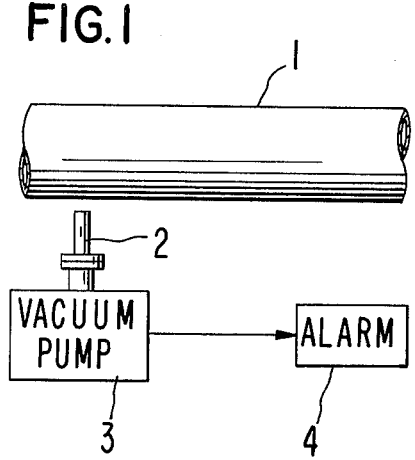
FIG. 1 is a schematic view of a system disclosing the basic concept of the invention.

The basic concept of this invention can be appreciated by consideration of FIG. 1 which illustrates a section of pipe 1 of the heat transfer system of a sodium-cooled nuclear reactor, and probe 2 of a sputter-ion pump 3 which is shown connected to an alarm device 4. A hydrogen compound, wherein the hydrogen is displaceable by sodium, is required in communication with the external surface of pipe 1 through which liquid sodium flows in the process of cooling the nuclear reactor. When a leak occurs in pipe 1, sodium comes into contact with the hydrogen compound existing in communication with the situs of the leak. A chemical reaction then takes place according to the general chemical equation

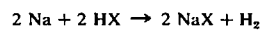

where X represents that element or radical of the hydrogen compound HX which combines with the sodium. As a result of this chemical reaction, hydrogen gas is generated. Since hydrogen is extremely mobile, the probe 2 can be placed a substantial distance from pipe 1 although as a practical matter it should be in the same room as the pipe. Of course a plurality of probes can be used and they can be connected to the same or separate pumps 3. The plural probes would be connected to separate pumps if it is desired to know which probe detected the leak or detected the leak first, assuming all the probes are not equally accessible to the leak. This arrangement will help locate the leak.

Figure 2:
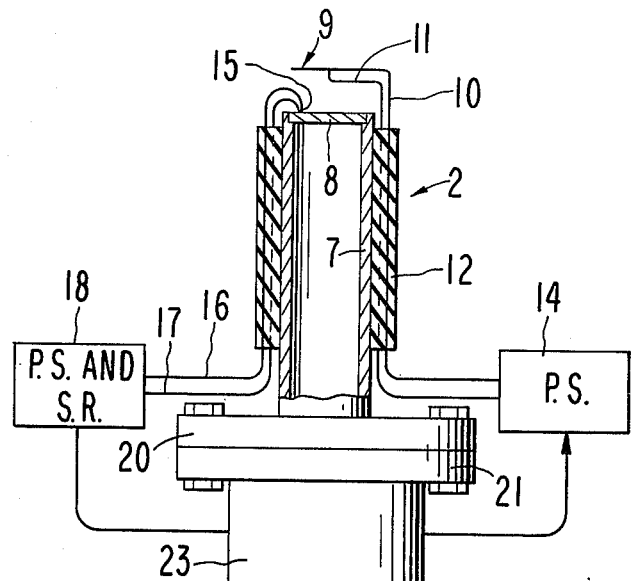
FIG. 2 is an enlarged cross-sectional view of the leak probe and shows other parts schematically.

FIG. 2 is an enlarged cross-sectional view showing the details of a suitable probe 2. The probe comprises a metal cylinder 7 having a hydrogen permeable diaphragm 8 brazed or otherwise sealed vacuum tight in the end thereof. The diaphragm is preferably made of palladium because of its high permeability to hydrogen gas, but other materials which are permeable to hydrogen and substantially non-permeable to other gases can be used, such as iron, nickel, titanium, zirconium, columbium and yttrium. As previously stated, the permeability of the diaphragm is a function of its temperature. More specifically the permeability increases with increase in temperature. Thus, it is desirable to run the diaphragm hot to increase the sensitivity of the system for a given size diaphragm. The diaphragm can be heated by a heater 9 when the diaphragm is located in a relatively cool environment. The heater can be a conventional spiral filament electric heater having an outer lead 10 and a center lead 11. An electrically insulating sleeve 12 surrounds the metal cylinder 7 to receive the leads 10 and 11. Heater 9 is energized in conventional manner by an electrical power supply 14.

It should be understood from previous discussion herein that a heater can serve one or both of two purposes. One purpose is simply to run the diaphragm hot in instances where the diaphragm is in a relatively cool environment. The other purpose is to maintain the temperature of the diaphragm constant so that the amount of hydrogen permeating through the diaphragm will truly reflect the concentration of hydrogen gas outside the probe. For a given concentration of hydrogen a relatively small amount will pass through the diaphragm at low temperature and a relatively large amount will pass at a high temperature of the diaphragm. In the embodiment of FIG. 2 the heater 9 is used for both purposes. Accordingly a temperature probe such as a thermocouple 15 is connected to the diaphragm 8. Thermocouple leads 16 and 17 go to a conventional power supply and a signal receiver 18. The temperature signal obtained by receiver 18 is transmitted to power supply 14 to adjust the power supply to maintain the diaphragm at a desired constant temperature, such as 400°C.

The lower end of the probe cylinder 7 is connected to vacuum pump 3. The connection is preferably made by a vacuum flange 20 sealed vacuum tight to pipe 7 and bolted to a mating flange 21 sealed vacuum tight to the inlet tube 23 to the vacuum pump 3. Suitable vacuum flanges are disclosed in U.S. Pat. No. 3,208,758.

As previously explained, vacuum pump 3 is preferably a sputter-ion pump because such a pump serves both as a pump and a pressure gauge. U.S. Pat. Nos. 2,755,014 and 2,993,638 disclose suitable sputter ion pumps. In this type of pump, the gas in the pump is ionized and the current drawn by the pump provides a measurement of the gas pressure in the pump. The gas pressure signal given by the pump current is transmitted to the alarm 4 of appropriate conventional design which will give an audio and/or visual alarm. In some systems it will be desirable for the alarm to also trigger an automatic device to shut down the nuclear reactor or other primary system being monitored for leaks. It is also desirable for the alarm device 4 to include a recorder which can be inspected to learn the magnitude and preferably the time of the leak.

In operation in this invention, the background pressure within pump 3 is maintained constant under continuous operating conditions. The alarm is set so the pressure signal from the pump to the alarm for this background pressure is insufficient to trigger the alarm, and any recorder in the alarm will record the background pressure as a zero or low level reading. When alkali metal, such as sodium, leaks out of its containment structure represented by pipe 1 and comes into contact with a hydrogen containing substance such as moisture containing air, hydrogen gas will be generated. The hydrogen gas will diffuse through diaphragm 8 into pump 3 where it will be ionized. The current drawn by the pump will then increase from the background level and will activate the alarm.

Although ion pumps of the type disclosed in U.S. Pat. Nos. 2,755,014 and 2,993,638 are preferred, it will be understood that other types of ionic pumps which give pressure measurement as well as perform pumping can be used. It will also be understood that vacuum pumps which merely pump can also be used if a conventional vacuum gauge is connected to the pump. In such case the alarm 4 would be connected to the vacuum gauge.

Where pipe 1 is surrounded by an atmosphere of air, it has been found that there will be sufficient water vapor in the air (everywhere the dew point of the air is as low as $-45°F$) to yield a detectable amount of hydrogen gas in the event of a sodium leak. Two reactions occur in this case: first, the sodium reacts with the water vapor according to the equation

and then, additional sodium will react with the sodium hydroxide so produced, according to the equation

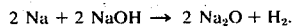

In situations where the presence of water vapor laden air in communication with the external surface of a sodium containment structure cannot be anticipated, the invention provides for disposing some other hydrogen containing substance in communication with said surface. In general the following and other substances of the type having hydrogen replaceable by an alkali metal are suitable: inorganic hydroxides, many clays (including silicates and oxides), insulating materials such as mica and asbestos, and organic compounds such as alcohols and phenols.

Where the invention is employed to detect leaks in nuclear reactor operation, the high temperatures and radiation fluxes inherent in nuclear reactors make it important that the hydrogen compound be stable at such high temperatures and radiation fluxes and be compatible with the stainless steel (or other high-temperature ferrous alloy) structural materials of the reactor heat transfer system. It has been found experimentally that barium hydroxide $Ba(OH)_2$ is especially suitable for disposition adjacent the external surfaces of a nuclear reactor coolant system. Barium hydroxide is chemically stable to temperatures of up to 700°C, which is well above the range at which nuclear reactors can safely operate. Barium hydroxide is also stable under neutron fluxes of up to $5 \times 10^{10}$ neutrons/cm$^2$/sec, gamma rays having energy levels up to 4 MeV, and beta particles having energies of up to 4 MeV. In addition, barium hydroxide will react with sodium according to the overall equation

or

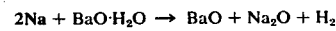

over the entire range of temperatures from the melting point of sodium up to 700°C. Furthermore, barium hydroxide will not react corrosively with stainless steel or other high-temperature ferrous alloys and is inert with respect to the silicates or oxides normally used as insulating materials.

Barium hydroxide is a relatively inexpensive substance that is commercially available in powdered form. It may be disposed in contact with the external surface of a sodium containment structure by being dissolved in water or suspended in water with a thickening agent such as bentonite clay. This solution or slurry may then be applied directly to the surface of the sodium containment structure as by painting or evaporation deposition. Alternatively, the barium hydroxide may be deposited by the same or similar methods upon metallic cloth, mesh material, or metal turnings, and the material so formed may be disposed in contact with the external surface of the sodium containment structure.

Figure 3:
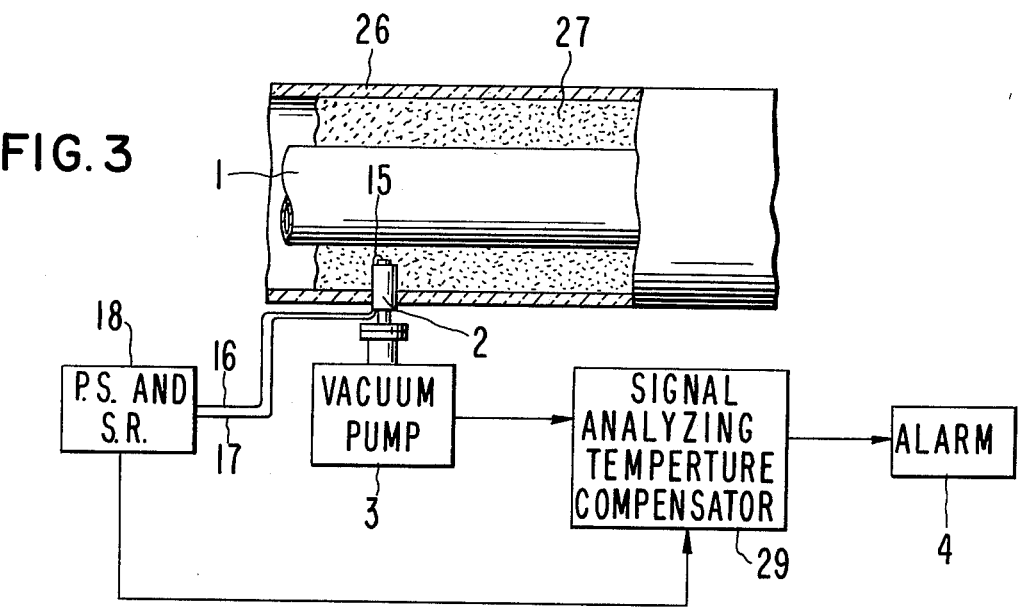
FIG. 3 discloses another embodiment of the invention partly in cross-section and partly schematically.

FIG. 3 discloses an embodiment in which the alkali metal containing pipe 1 is surrounded by a thermal insulation pipe 26, and the intervening space is provided with a porous filling 27 of metal turnings coated with barium hydroxide as previously described. Probe 2 is inserted through the insulation pipe 26 and into the space containing metal turnings 27. Since the diaphragm in probe 2 in this embodiment is within the thermally insulated hot space surrounding tube 1, heater 9 is omitted because it is not needed for the purpose of running the diaphragm hot. For example, liquid sodium in a nuclear reactor system will not be at some high temperature such as 400°C. If the system is such that the temperature of the alkali metal will vary, it is necessary to compensate for the second purpose of the missing heater; namely, maintaining the diaphragm at a constant temperature. This is accomplished by transmitting the temperature signal from receiver 18 to a signal analyzing temperature compensator 29. Compensator 29 analyzes the temperature signal from receiver 18 and generates a correction of the pressure signal from pump 3 in order to transmit a temperature-corrected pressure signal to alarm 4. More specifically the leak detecting system is calibrated to activate alarm 4 if a selected concentration of hydrogen is present outside diaphragm 8 when the diaphragm is at a selected temperature such as 400°C. Compensator 29 is calibrated with reference to well known data on diffusion rate as a function of diaphragm temperature. For example the diffusion rate of palladium as a function of temperature is given in "Permeation of Hydrogen Through Metals", R. W. Webb, Report No. NAA-SR-10462, Atomics International Report AT(11-1)-GEN-8, July 25, 1965. The calibration of compensator 29 is such that if it receives a temperature signal of the selected temperature from receiver 18 it will transmit to alarm 4 the pressure signal from pump 3 without adjustment. However, if the temperature of the diaphragm goes above or below the selected temperature, this different temperature signal will cause the compensator 29 to adjust the pressure signal from pump 3 down or up, respectively, so that the ultimate pressure signal to alarm 4 will represent the pressure which would appear in the pump if the diaphragm were at the selected pressure.

Figure 4:
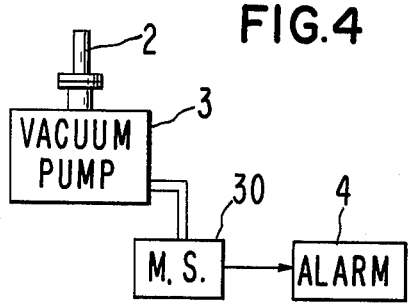
FIG. 4 is a schematic view of a system embodying a mass spectrometer.

In situations where ambient non-isotopic hydrogen gas might normally be present in the vicinity of the sodium containment structure, e.g., where welding operations might take place in the vicinity of the nuclear reactor or other basic systems being monitored, it will be necessary that the hydrogen gas sensor distinguish between the ambient hydrogen and that which is generated by an alkali metal leak. This can be accomplished by disposing a compound containing a hydrogen isotope in communication with the external surface of the alkali metal containment structure and by coupling the vacuum pump to mass spectrometer. The isotope containing compound is coated on the pipe 1 or on other material as described for barium hydroxide in connection with FIG. 3. Barium deuteroxide (i.e., barium hydroxide with a heavy hydrogen atom) has essentially the same stability characteristics of barium hydroxide, and is readily available for commercial uses. For this reason, barium deuteroxide is an especially suitable compound for disposition in the vicinity of a nuclear reactor. Upon the occurrence of a sodium leak, the sodium will react with the barium deuteroxide to generate deuterium gas. The region in the vicinity of the situs of the leak will immediately fill with a quantity of deuterium gas greatly in excess of the amount of deuterium gas normally found in the atmosphere. This excess can be detected by a mass spectrometer, and the output signal of the spectrometer is transmitted to the alarm and recording device. FIG. 4 shows an arrangement in which a mass spectrometer 30 is coupled to pump 3, and the output from the spectrometer is transmitted to the alarm 4. Where sodium leak detection is based upon the sensing of a hydrogen isotope gas by a spectrometer, it is not essential that the vacuum pumping means provide a method for monitoring the pressure within the pump. Thus, any type of high vacuum pump would be suitable although a sputterion pump as defined above is still desirable but the pump current is not used as the pressure signal. Also a mass spectrometer can be used to detect non-isotopic hydrogen instead of using pump current or a vacuum gauge, where the gas to be detected is nonisotopic hydrogen. Any conventional mass spectrometer can be used which is designed or adjusted to selectively detect the form of hydrogen gas which is to be measured. Although the mass spectrometer is shown connected directly to the alarm 4 it could be connected to the temperature compensator 29.

Various changes could be made in the structures and embodiments shown herein without departing from the concept of the present invention. Such changes are within the scope and spirit of this invention to the extent that they are covered by the following claims.

What is claimed is:

1. A method of determining whether or not an alkali metal leak exists in a structure confining the alkali metal comprising the steps of:

exposing the exterior of said structure to a substance including hydrogen in a form chemically replaceable by said alkali metal to form hydrogen gas;

detecting any of said formed hydrogen gas exterior to said structure with a hydrogen gas detection apparatus which provides a signal when said hydrogen is detected; and evaluating said signal to determine whether or not said alkali metal leak exists.

2. In a containment structure containing a liquid alkali metal heat exchange fluid circulating in said structure, a method of detecting whether or not there is a leak of the alkali metal to the exterior of said structure comprising the steps of:

supplying a substance containing hydrogen in a form chemically replaceable by said alkali metal outside of and in proximity to said structure;

combining any leaking alkali metal with said substance to generate hydrogen gas;

detecting the presence or absence of any generated hydrogen gas outside said structure;

generating an output signal indicative of the presence or absence of said generated hydrogen gas; and evaluating said output signal to determine whether or not said alkali metal leak exists.

3. The method of claim 2 wherein said hydrogen including substance is a gas containing water vapor.

4. The method of claim 2 wherein a hydrogen gas detector is provided to detect the formed hydrogen gas, said step of detecting further including the steps of measuring the temperature of a hydrogen gas permeable wall portion of the hydrogen gas detector, the detector producing an indication as a function of the temperature of the wall portion, and compensating the hydrogen gas detector in accordance with said measured temperature so that the indication is substantially independent of the temperature of the wall portion.

5. The method of claim 2 wherein said formed and detected hydrogen gas is deuterium.

6. The method of claim 5 including the step of measuring the presence of said formed deuterium with a mass spectrometer.

7. The method of claim 2 wherein said step of detecting further includes the step of heating a hydrogen gas permeable wall portion of a hydrogen gas detecting apparatus.

8. The method of claim 7 wherein the step of heating further includes the step of maintaining the temperature of said hydrogen gas permeable wall portion at a substantially constant, desired temperature.

9. In combination:
a containment structure;
a heat exchange, alkali metal fluid circulating in said structure; and
a detector mounted outside of and in proximity to the exterior of said structure for detecting a reaction of any of said fluid leaking through said structure with a substance including hydrogen in a form chemically replaceable by said alkali metal, said substance being in proximity to said detector and in communication with the exterior of said structure.

10. The combination of claim 9 including alarm means responsive to said detector for indicating a presence of said leak to be detected.

11. The combination of claim 9 wherein said hydrogen including substance is water vapor.

12. The combination of claim 9 wherein said formed and detected hydrogen gas is deuterium, and said detecting means includes a mass spectrometer.

13. The combination of claim 9 wherein said containment structure is surrounded by a thermal insulation pipe, a space being formed between said containment structure and said pipe, said space containing said hydrogen including substance, said hydrogen gas detector being supported by said pipe.

14. The combination of claim 9 wherein said detector includes a sputter-ion pump.

15. The combination of claim 14 wherein said hydrogen gas detector comprises a sealed chamber, a wall portion of said chamber being permeable to hydrogen gas, and means for indicating the presence of said hydrogen gas permeating into said chamber through said wall portion.

16. The combination of claim 15 wherein said hydrogen gas detector includes means for sensing the temperature of said hydrogen gas permeable wall portion and for generating a signal indicative of said temperature; means for generating a signal indicative of the pressure of said hydrogen gas in said chamber, said last named means deriving the pressure indicative signal as a function of the temperature of the wall portion, and compensating means responsive to said temperature indicative signal for compensating the pressure indicative signal generating means so that the pressure indicative signal is temperature corrected.

17. The combination of claim 15 wherein said hydrogen gas detector further includes means for heating said hydrogen gas permeable wall portion.

18. The combination of claim 17 wherein said hydrogen gas detector further includes means for maintaining said hydrogen gas permeable wall portion at a constant desired temperature.

19. Apparatus for detecting a liquid alkali metal leak, comprising a containment structure containing an alkali metal fluid circulating in said structure, the exterior of said structure being in communication with a substance including hydrogen in a form chemically replaceable by said alkali metal, whereby in the event of the leak, hydrogen gas is formed externally of said structure; means for detecting the presence or absence of any of said formed gas, said detecting means being positioned outside of and in proximity to said structure for determining the presence or absence of the leak; and means responsive to the detecting means for enabling the presence or absence of said leak to be detected.

20. The apparatus of claim 19 further including a thermal insulation pipe surrounding said containment structure, a space being provided between said containment structure and said pipe, said space containing said hydrogen including substance therein, said hydrogen gas detector being supported by said pipe.

21. The apparatus of claim 19 wherein said hydrogen gas detector includes means for sensing the temperature of said hydrogen gas permeable wall portion and for generating a signal indicative of said temperature; means for generating a signal indicative of the pressure of said hydrogen gas in said chamber; and compensating means for receiving said temperature and pressure indicative signals to provide a temperature-corrected output signal.

22. The apparatus of claim 19 wherein said detecting means comprises a sputter-ion pump in gaseous communication with said hydrogen forming substance.

23. The apparatus of claim 19 wherein said detecting means comprises a sealed chamber, a wall portion of said chamber being permeable to said formed hydrogen gas.

24. The apparatus of claim 23 including means for heating said hydrogen permeable wall portion of said chamber.

25. The apparatus of claim 24 further including means for maintaining said hydrogen permeable wall portion of said chamber at a constant desired temperature.

* * * * *